(12) United States Patent
Ishihara et al.

(10) Patent No.: US 7,377,642 B2
(45) Date of Patent: May 27, 2008

(54) FUNDUS CAMERA

(75) Inventors: Mutsutaka Ishihara, Itabashi-ku (JP);
Taisaku Kogawa, Itabashi-ku (JP)

(73) Assignee: Kabushiki Kasisha Topcon, Tokyo (JP)

( * ) Notice: Subject to any disclaimer, the term of this patent is extended or adjusted under 35 U.S.C. 154(b) by 133 days.

(21) Appl. No.: 11/498,728

(22) Filed: Aug. 4, 2006

(65) Prior Publication Data
US 2007/0030451 A1  Feb. 8, 2007

(30) Foreign Application Priority Data
Aug. 5, 2005  (JP) .............................. 2005-227825

(51) Int. Cl.
*A61B 3/14*  (2006.01)
*A61B 3/10*  (2006.01)

(52) U.S. Cl. ...................... 351/206; 351/205

(58) Field of Classification Search ........ 351/203–223, 351/239, 245, 246
See application file for complete search history.

(56) References Cited

U.S. PATENT DOCUMENTS 4,538,889 A   9/1985 Heine et al. ................ 351/205
5,617,156 A * 4/1997 Sano et al. ................. 351/214
6,575,571 B2* 6/2003 Shibata ...................... 351/206
2003/0208125 A1 11/2003 Watkins ..................... 600/473
2004/0174498 A1  9/2004 Zorn et al. .................. 351/214

FOREIGN PATENT DOCUMENTS

JP      07-39523 A    2/1995
JP      09-66032 A    3/1997
JP   2000-262478 A    9/2000

* cited by examiner

*Primary Examiner*—M. Hasan
(74) *Attorney, Agent, or Firm*—Buchanan, Ingersoll & Rooney, P.C.

(57) ABSTRACT

A fundus camera which includes an illumination optical system for projecting an illumination light to a fundus of a subject's eye: a photographing device for photographing the fundus; and light-receiving optical systems, which include a focus lens disposed in a light-receiving optical path for focusing the photographing devices with respect to the fundus and diopter compensation lenses disposed for being inserted into or withdrawn from the light-receiving optical path for guiding reflected light from the fundus to the photographing devices; a controlling device for determining whether a feasible focusing range of the focus lens is surpassed; and driving devices for inserting the diopter compensation lenses into or withdrawing them from the light-receiving optical path. The controlling device controls the driving devices in a defined manner.

5 Claims, 11 Drawing Sheets

FUNDUS CAMERA

The present application claims the priority benefit of Japanese Patent Application 2005-227825 filed on Aug. 5, 2005, the contents of which are incorporated herein by reference.

BACKGROUND OF THE INVENTION

1. Field of the Invention

The present invention relates to an optical fundus camera having a diopter compensation lens to compensate a diopter scale with respect to a fundus of a subject's eye.

2. Description of the Prior Art

Conventionally, there is known a fundus camera including an illumination optical system for projecting an illumination light to a subject's eye fundus, an observing optical system for guiding the reflected illumination light from the fundus to a first photographing device, and a photographing optical system for guiding the reflected illumination light from the fundus to a second photographing device.

According to Japanese Patent Application Laid Open Nos. 2000-262478 and H9-66032, it is known that such fundus camera includes a stick mirror which may be inserted into or withdrawn from an optical path of the illumination optical system and a focus-target projecting optical system for projecting focus-target light split into two bundles by the stick mirror and the illumination optical system to the fundus.

In such fundus camera, it is determined that the fundus camera is out of focus if two focus-target images formed from the two split bundles of the focus-target light are positioned separately side by side, and the fundus camera is in a focused state if the two focus-target images are lined up vertically.

After a main body of the fundus camera is aligned with respect to the subject's eye fundus, a light-receiving optical system is focused by operations on a focus handle, etc., to shift a focus lens disposed in the light-receiving optical system along an optical axis of the light-receiving optical system.

While in the above described fundus camera, a focusing range of the focus lens is set in a feasible diopter compensation range for a normal person. However, the subject's eye may be of either severe myopia or hyperopia. Thus, it is impossible to conjugate the fundus of the subject's eye with a photographing element even though there are performed focus operations with respect to the fundus of the subject's eye when the subject's eye is of severe myopia or hyperopia.

According to Japanese Patent Application Laid Open No. H7-39523, in order to solve the above problem, there is also known a fundus camera in which diopter compensation lenses enabling a feasible focus of the focus lens are inserted into a light-receiving optical path of an observing and/or a photographing optical system in a case when the subject's eye is of either severe myopia or hyperopia.

However, a subject will not be discovered to be of severe myopia or hyperopia unless it is impossible to have the focus lens focused on the fundus through practical attempts on operating the focus lens while observing the fundus of the subject's eye. And only after that may a diopter compensation lens be manually inserted into the light-receiving optical path. Thus, it costs more time to obtain a photograph for the fundus.

SUMMARY OF THE INVENTION

It is, therefore, an object of the present invention in view of the aforementioned problems to provide a fundus camera in which a diopter compensation lens with a diopter scale relating to a subject's eye is inserted into a light-receiving path if the subject's eye is of either severe myopia or hyperopia.

To achieve the aforementioned object, the fundus camera according to the present invention comprises an illumination optical system for projecting an illumination light to a fundus of a subject's eye; a photographing device for photographing the fundus; a light-receiving optical system, which includes a focus lens disposed in a light-receiving optical path for focusing the photographing device with respect to the fundus and a diopter compensation lens disposed for being inserted into or withdrawn from the light-receiving optical path, for guiding the reflected illumination light from the fundus to the photographing device; and additionally, a controlling device for determining whether a feasible focusing range of the focus lens is surpassed or not; and a driving device for inserting the diopter compensation lens into or withdrawing the diopter compensation lens from the light-receiving optical path, wherein the controlling device initializes and controls the driving device to insert into the light-receiving optical path the diopter compensation lens with a suitable diopter scale making the focus lens focus feasibly if the feasible focusing range of the focus lens is surpassed.

According to the aforementioned configuration, the controlling device will initialize and control the driving device to insert into the light-receiving optical path the diopter compensation lens with a suitable diopter scale making the focus lens focus feasibly if the feasible focusing range of the focus lens is surpassed.

That is to say, the controlling device controls inserting the diopter compensation lens with respect to the diopter scale of the subject's eye into the light-receiving path to make a feasible focus on the fundus when the subject's eye is of either severe myopia or hyperopia.

It is preferable to insert the diopter compensation lens into the light-receiving path either automatically via the driving device or manually.

BRIEF DESCRIPTION OF THE DRAWINGS

FIG. 3A (b) is an explanatory view showing a light intensity of a cross section along a line A2-A2 in FIG. 3A (a).

FIG. 3A (c) is an explanatory view showing a light intensity of a cross section along a line A3-A3 in FIG. 3A (a).

FIG. 3B (b) is an explanatory view showing a light intensity of a cross section along a line A4-A4 in FIG. 3B (a).

FIG. 3B (c) is an explanatory view showing a light intensity of a cross section along a line A5-A5 in FIG. 3B (a).

DETAILED DESCRIPTION OF THE INVENTION

[Configurations]

Figure 1:
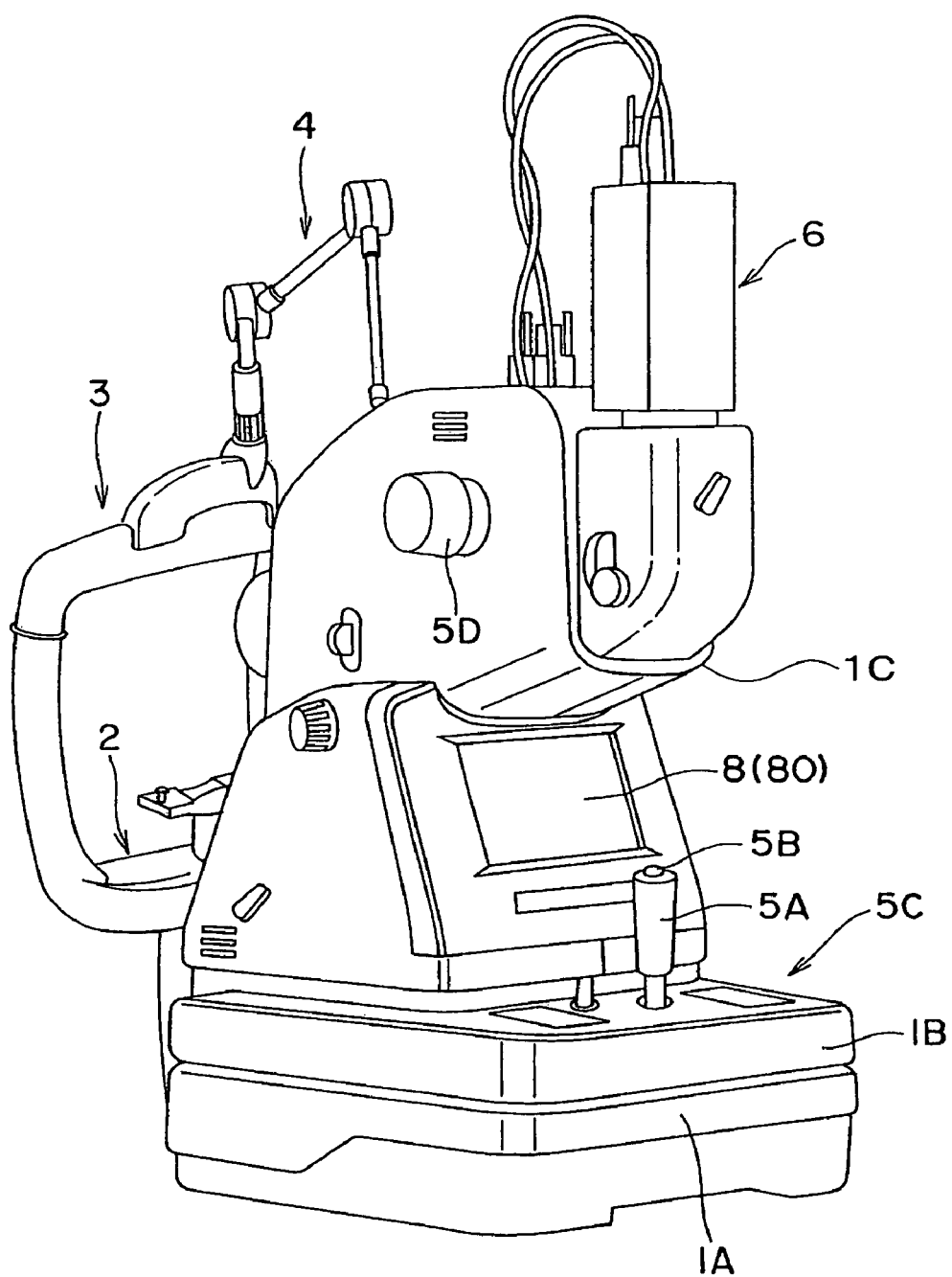
FIG. 1 is an outline view showing a fundus camera according to the present invention.

An outline view of a non-mydriatic type fundus camera according to the present invention, as an example of an ophthalmologic photographing apparatus, is shown in FIG. 1.

In FIG. 1, reference numerals 1A, 1B, 1C, 2 and 3 represent a base, a mount pedestal, a main body, a chin holder and a forehead pad of the fundus camera, respectively; and reference numerals 4, 5A, 5B, 5C, 5D and 6 represent an external fixation light, a joystick, a photographing switch, an operation panel disposed on the mount pedestal 1B, a focus handle and a electronic photographing device of the fundus camera, respectively.

The fundus camera may be operated not only by the joystick 5A, the photographing switch 5B, various buttons or switches on the operation panel 5C and the focus handle 5D, but also from a monitor screen 80 of a displaying device such as a monitor 8 using a mouse (not shown).

Hereinafter, the joystick 5A, the photographing switch 5B, the operation panel 5C, the focus handle 5D, the mouse (not shown), the monitor 8 and other power source or operation switches are generally referred to as an operation device 5.

The electronic photographing device 6 includes a photographing TV camera 6A having a photographing element 6a, for example a CCD as a photographing unit, and an observing TV camera 6B having a photographing element 6b, for example a CCD as a photographing unit.

The photographing element CCD 6a is connected to the monitor 8 via a photograph recording device, for example a still video recorder 7 and a controlling device 9. The photographing element CCD 6b is connected to the monitor 8 via the controlling device 9.

Figure 2:
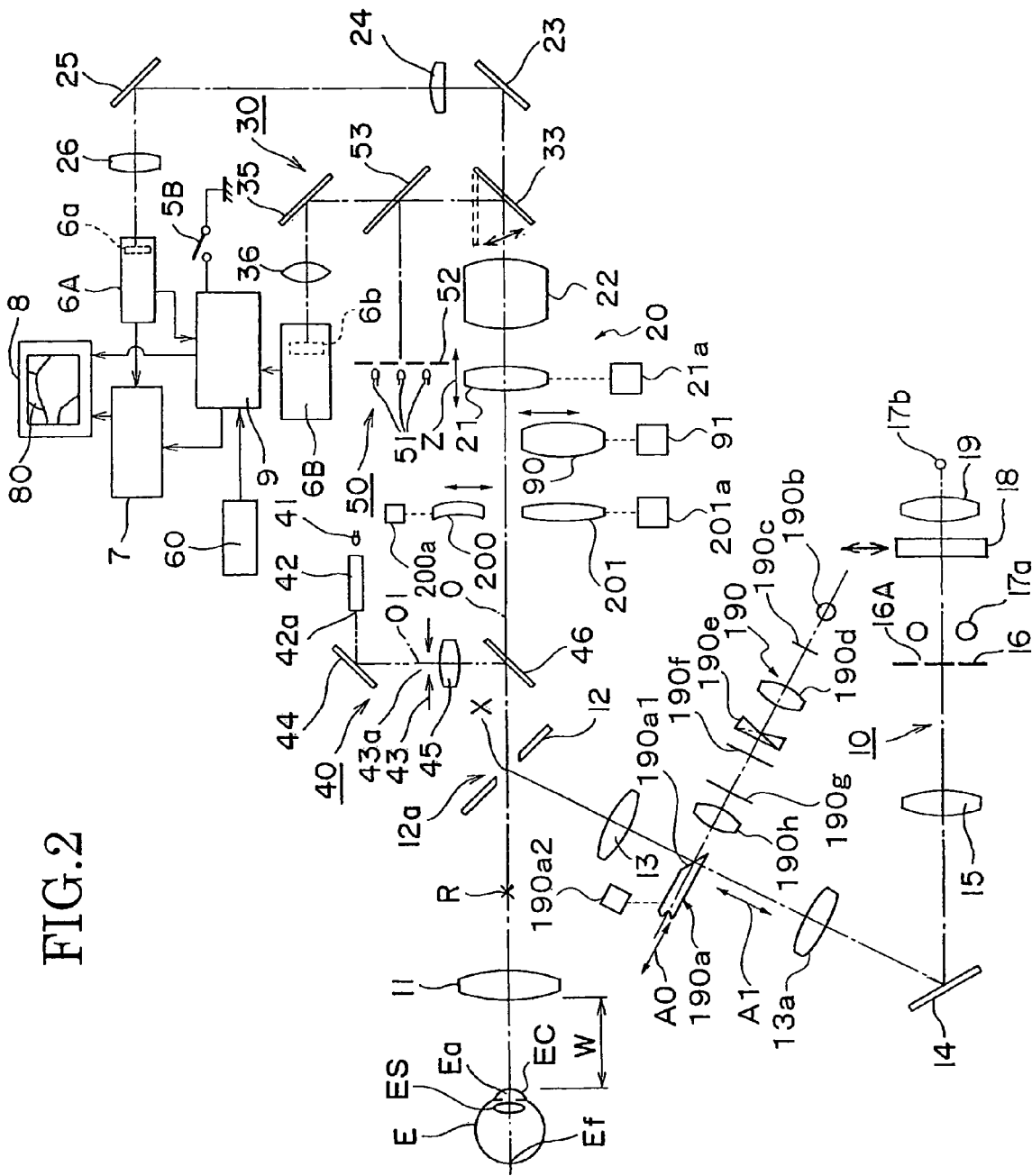
FIG. 2 is a view showing optical systems of the fundus camera according to the present invention.

As shown in FIG. 2, inside the main body 1C, there are disposed with an illumination optical system 10 for illuminating a fundus Ef of a subject's eye E, a photographing optical system 20 for photographing the fundus Ef, an observing optical system 30 for observing the fundus Ef, an alignment target projecting optical system 40 for aligning the main body 1C relative to the subject's eye E, and an inner fixation target projecting optical system 50 for projecting fixation targets to the fundus Ef to fix the subject's eye E.

[The Illumination Optical System 10]

The illumination optical system 10, an optical system which illuminates the fundus Ef with an infrared light during observation and visual lights during photographing, includes an object lens 11, a perforated mirror 12, a relay lens 13, a relay lens 13a, a reflecting mirror 14, a relay lens 15, a ring-aperture plate 16 with a ring-aperture conjugating with a pupil Ea of the subject's eye E, an xenon lamp 17a as a photographing light source, an infrared filter (Hereinafter as IR filter) 18, a condenser lens 19 and a halogen lamp 17b as an observing light source.

In addition, a distance W is a distance where the perforated mirror 12 will be in a position conjugating with a cornea Ec of the subject's eye E if the object lens 11 is disposed at the proper operation distance W from the subject's eye E.

A stick mirror or target stick 190a included in a focus target projecting optical system 190 is configured in such a way that the stick mirror 190a may be inserted into or withdrawn from an optical path of the illumination optical system 10 at a position optically conjugated with the fundus Ef of the subject's eye E.

The focus target projecting optical system 190 includes sequentially a target projecting light source 190b, a pinhole plate 190c, a lens 190d, a prism lens 190e, a focus target plate 190f, a biforate stop plate 190g, a lens 190h and the stick mirror 190a.

Thus, focus target light from the target projecting light source 190b transmits through the pinhole plate 190c, the lens 190d, the prism lens 190e, the focus target plate 190f, the biforate stop plate 190g and the lens 190h to the stick mirror 190a, and is reflected from a reflecting surface 190a1 of the stick mirror 190a to be projected to the fundus Ef of the subject's eye E through the relay lens 13, the perforated mirror 12 and the object lens 11.

The reflecting surface 190a1 of the stick mirror 190a is also conjugated with the focus target plate 190f. Furthermore, the stick mirror 190a is disposed in such a way that it may be inserted into or withdrawn from the optical path of the illumination optical system 10 along an arrowed direction A0 as shown in FIG. 2 through a driving device 190a2, such as a pulse motor or a solenoid etc.

The focus target light are split into two bundles by the prism lens 190e and biforate stop plate 190g etc. Two focus target images 191a and 191b separated from side to side as shown in FIG. 12 will be observed if the fundus Ef of the subject's eye E is not conjugated with the stick mirror 190a.

Figure 10:
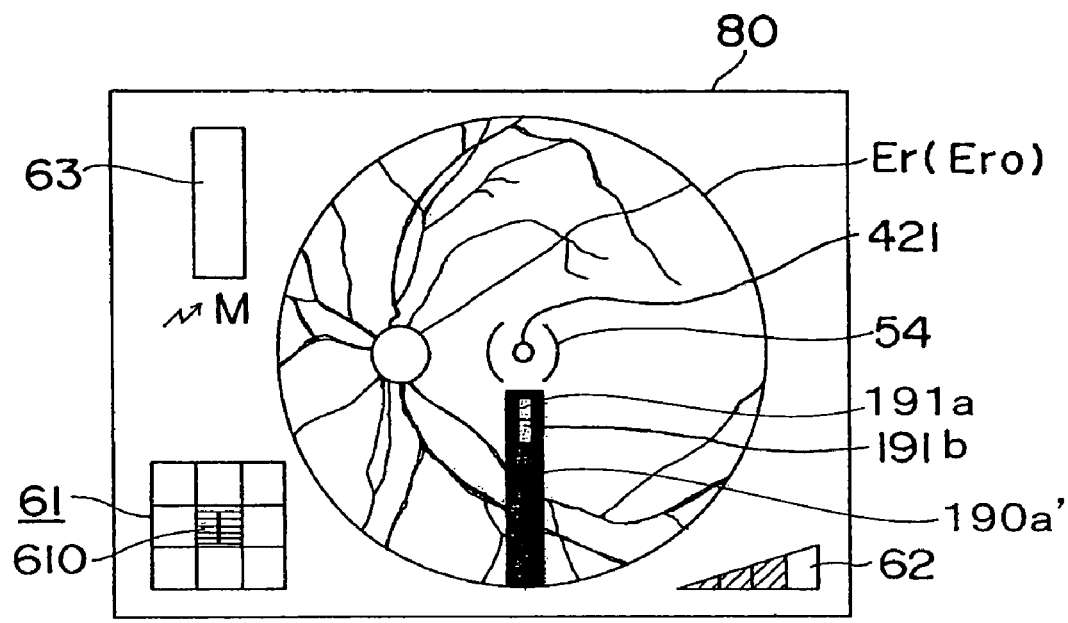
FIG. 10 is an explanatory view showing the monitor screen in which a photographed image of a central region of the fundus is displayed.

Thus, it is possible for a physician to perform focusing easily and quickly only by lining up vertically the two separated focus target images 191a and 191b into one as shown in FIG. 10.

In addition, in order to keep the focus target plate 190f and the fundus Ef conjugating constantly with each other, the focus target projecting optical system 190 is shifted along an axis of the optical path of the illumination optical system 10 in an arrowed direction A1 as shown in FIG. 2 in conjunction with a focus lens 21 (To be described hereinafter) included in the photographing optical system 20 and observing optical system 30.

Figure 3:
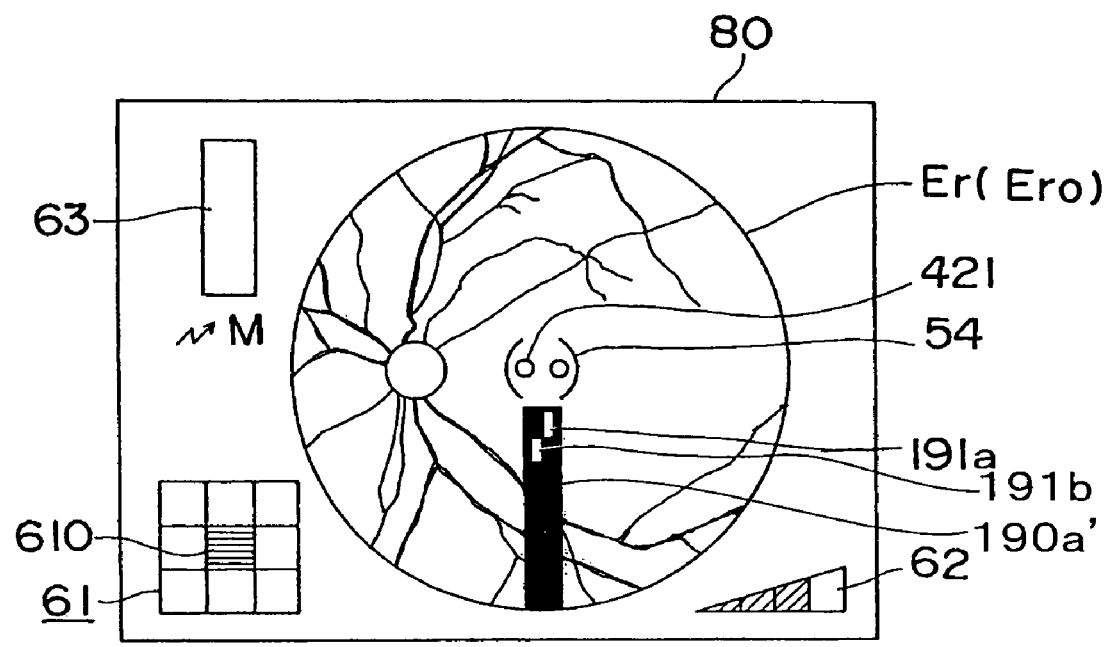
FIG. 3 is an explanatory view showing a monitor screen in which a photographing region is displayed animatedly.
Figure 12:
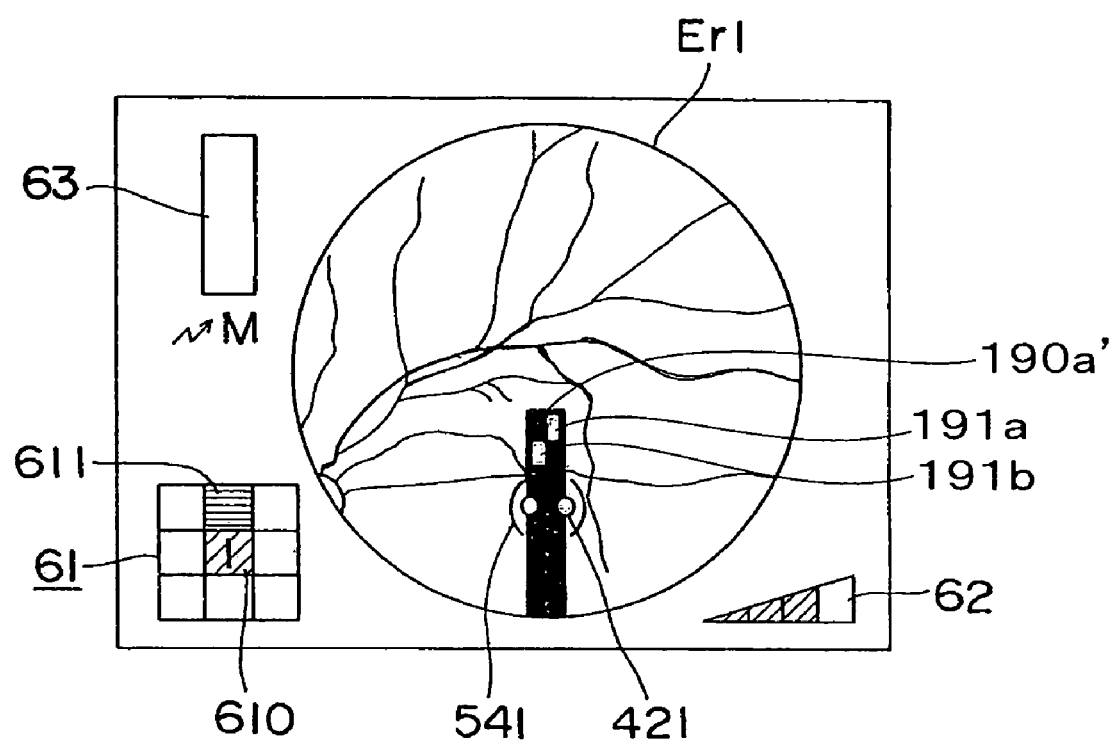
FIG. 12 is an explanatory view showing the monitor screen in which a photographed image of the peripheral regions of the fundus is displayed.

Therefore, the focus target projecting optical system 190 is so configured that if the fundus Ef and the focus target plate 190f are not conjugated, the two focus target images 191a and 191b will be observed splitting from side to side as shown in FIGS. 3 and 12, and if the fundus Ef and the focus target plate 190f are conjugated, the two focus target images 191a and 191b will be observed lining up vertically into one as shown in FIG. 10, thus it is simple to perform focusing.

According to the above configuration, it is possible for the physician to determine that the fundus camera is focused if the two focus target images 191a and 191b from the focus target projecting optical system 190 displayed on the monitor screen 80 are lined up vertically into one and begin to perform photographing. Also, it is possible for the physician to adjust focus by observing the focus target images 191a and 191b.

[The Photographing Optical System 20]

The photographing optical system or light-receiving optical system 20, an optical system for taking still photographs of the fundus Ef illuminated by the illumination optical system 10, includes the object lens 11, the perforated mirror 12, the focus lens 21, an imaging lens 22, a reflecting mirror 23, a field lens 24, a reflecting mirror 25, a relay lens 26 and the photographing TV camera 6A.

The photographing element CCD 6a of the photographing TV camera 6A is kept conjugating with the fundus Ef optically. In addition, the focus lens 21 is configured to shift along an axis of a light-receiving optical path driven by a driving device 21a, for example a pulse motor.

It is preferable to use a gear mechanism including gears as a coupling mechanism to couple the focus target projecting optical system 190 with the focus lens 21.

It is preferable for the focus target projecting optical system 190 to be driven by a driving device such as a driving motor (not shown) to shift along the optical axis O of the optical path of the illumination optical system 10, it is also preferable to configure the driving motor in conjunction with the driving device 21a for diving the focus lens 21 to shift along the optical axis O.

Between a half-silvered mirror 46 (to be described hereinafter) and the focus lens 21, there are disposed with an auxiliary lens 90 and diopter compensation lenses 200 and 201 driven respectively by a driving device 91 and driving devices 200a and 201a such as pulse motors or solenoids etc to be inserted into or withdrawn from the light-receiving optical path or photographing optical path of the photographing optical system 20.

The auxiliary lens 90 is inserted into the photographing optical path when the fundus Ef and the photographing element CCD 6b of the observing TV camera 6B are conjugated through the focus lens 21 in order to make the CCD 6b conjugating with an eye lens Es of the subject's eye E after the alignment of the main body 1C or the object lens 11 relative to the subject's eye E is finished so that the object lens 11 is at the proper operation distance W from the subject's eye E.

At this moment, the photographing element CCD 6a of the photographing TV camera 6A is also conjugating with the eye lens Es of the subject's eye E.

It is preferable for the diopter compensation lens 200 to be a minus lens used to compensate severe myopia with a diopter scale of for example −20D and the diopter compensation lens 201 to be a plus lens used to compensate severe hyperopia with a diopter scale of for example +20D, or vice versa.

[The Observing Optical System 30]

The observing optical system 30, an optical system for observing the fundus Ef illuminated by the illumination optical system 10 by branching the photographing optical system 20 through a quick return mirror 33 interluded in the optical path of the photographing optical system 20, includes a reflecting mirror 35, a relay lens 36 and the observing TV camera 6B.

Furthermore, the photographing element 6b of the observing TV camera 6B is disposed with respect to the quick return mirror 33 conjugating with the photographing element 6a of the photographing TV camera 6A.

[The Alignment Target Projecting Optical System 40]

The alignment target projecting optical system 40, an optical system for projecting an alignment target toward the subject's eye E, includes a LED 41 as an alignment light source, a light guide 42 for guiding light from the LED 41, a reflecting mirror 44 for reflecting light from the light guide 42 to a biforate stop 43, a relay lens 45, the branching half-silvered mirror 46, the perforated mirror 12 and the object lens 11 from the photographing optical system 20.

Figure 4:
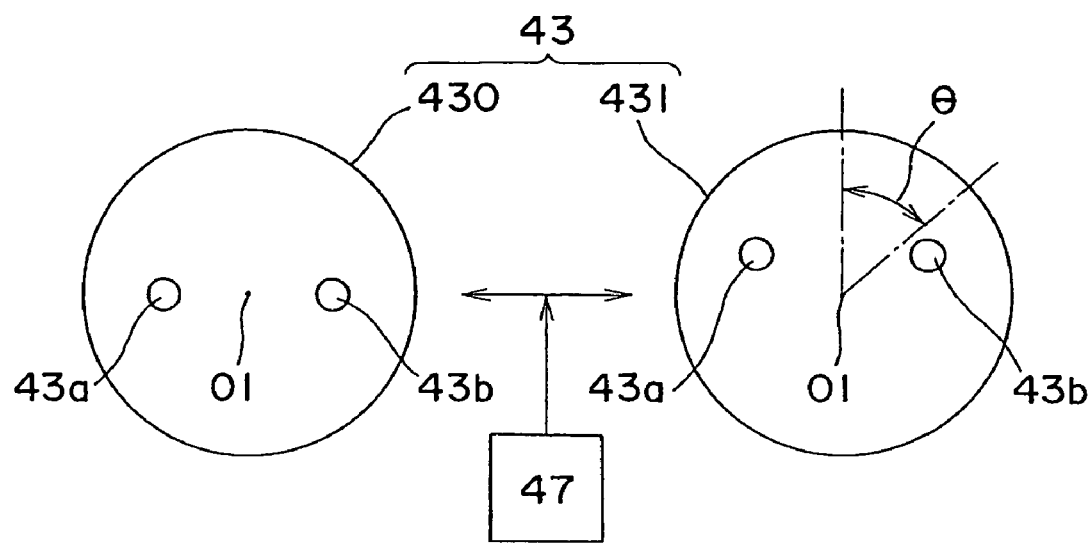
FIG. 4 is an explanatory view showing a relationship between 2-hole configuration of a biforate stop and a switching device 47 for switching the biforate stop.

The biforate stop 43 disposed adjacent to the relay lens 45 includes a biforate stop 430 for designating a central part of the fundus Ef and a biforate stop 431 for designating surrounding parts of the fundus Ef, as shown in FIG. 4. It is possible for the biforate stops 430 and 431 to be switched by a switching device 47 and inserted into the optical path by a solenoid etc (not shown).

Each of the biforate stops 430 and 431 has a pair of perforated portions 43a and 43b formed symmetrically with respect to an optical axis O1, while the perforated portions 43a and 43b of the biforate stop 431 are some distance further away from the optical axis O1 since the biforate stop 431 is used for designating the surrounding parts of the fundus Ef. Therefore, the distance between the central part and surrounding parts is determined.

In addition, it is possible for the biforate stop 431 used for designating the surrounding parts of the fundus Ef to rotate at a rotation angle θ around the optical axis O1 as rotation center along arrowed directions as shown in FIG. 4 when it is inserted into the optical path.

Therefore, it is possible for the alignment target projecting optical system 40 to project the alignment targets toward the subject's eye E with equal distance to the central part of the fundus Ef but different deviation angle by setting the rotation angle θ of the biforate stop 431. In this preferred embodiment, the rotation angle θ is set at 45 degrees, but it is also possible to set the rotation angle θ at any angle corresponding to a position of a fixation light source to be described hereinafter.

The half-silvered mirror 46 has a transmission characteristic which permits roughly a half transmission of light of a wavelength of 760 nm and a transmission of light of wavelengths other than 760 nm close to 100%, and thus will not have any attenuation affect on total amount of light other than 760 nm reflected from the fundus Ef.

The LED 41 has a light emitting characteristic for emitting near-infrared light of wavelengths around 760 nm. An emitting end 42a of the light guide 42 is disposed above the optical axis O1 of the relay lens 45 and the optical axis O of the photographing optical system 20. The biforate stop 43 is an optical device which splits an alignment image 421 based on alignment light and projects the separated images into the subject's eye E when the operation distance W is off from the proper position.

The alignment light emitted from the emitting end 42a of the light guide 42 is reflected by the reflecting mirror 44 and guided to the biforate stop 43. The alignment light penetrated the perforated portions 43a and 43b of the biforate stop 43 is guided to the relay lens 45.

The alignment light penetrated the relay lens 45 is reflected toward the perforated mirror 12 by the half-silvered mirror 46. The relay lens 45 forms a temporary image of the emitting end 42a which serves as an alignment target on an central position X of a perforated portion 12a of the perforated mirror 12, which is positioned at the optical axis 0 of the photographing optical system 20.

The pair of alignment light forming the alignment target at the central position X of the perforated portion 12a are guided to the cornea Ec of the subject's eye E through the object lens 11.

[The Inner Fixation Target Projecting Optical System 50]

The inner fixation target projecting optical system 50, an optical system for projecting fixation targets which are guided to the central part of the posterior fundus and the surrounding parts of the subject's eye E which is formed by branching the observing optical system 30 through a dichroic mirror 53 having an optical characteristic of transmitting infrared light and reflecting visual light, includes fixation light sources 51 such as emitting diodes etc, a mask plate 52 disposed opposing to the fixation light sources 51, and the dichroic mirror 53.

Figure 5:
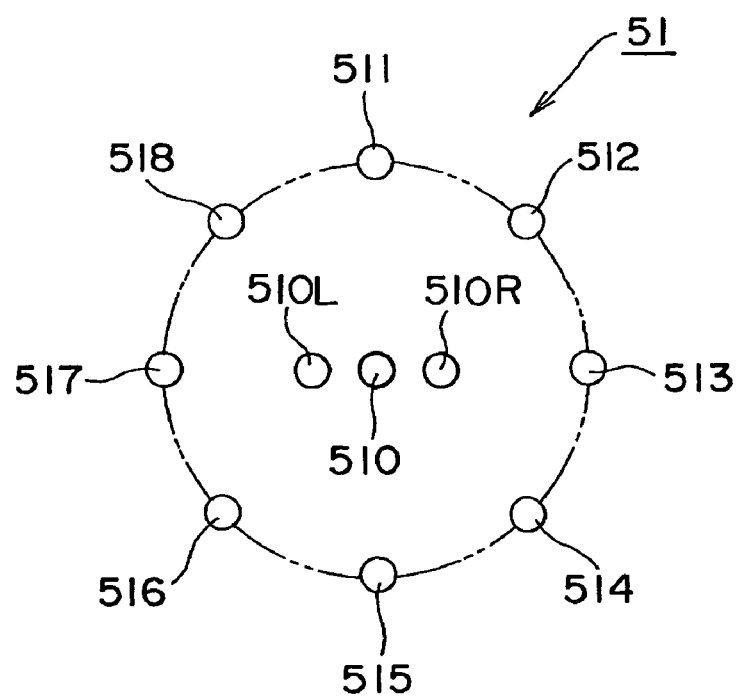
FIG. 5 is a view showing an arrangement state of luminous diodes as vision fixation light sources shown in FIG. 2.

The fixation light sources 51 as shown in FIG. 5, for example include centrally disposed fixation light source 510 and eight fixation light sources 511-518 evenly disposed in a circle around the fixation light sources 510.

The central fixation light source 510 is used to observe and/or photograph the fundus Ef around macula part and fixation light sources 510L and 510R are used to photograph an area determined by the Law of Health and Medical Services for the Aged in correspondence to the subject's left and right eye respectively.

The peripheral fixation light sources 511-518 are used to observe and/or photograph the surrounding parts of the fundus Ef.

Figure 6:
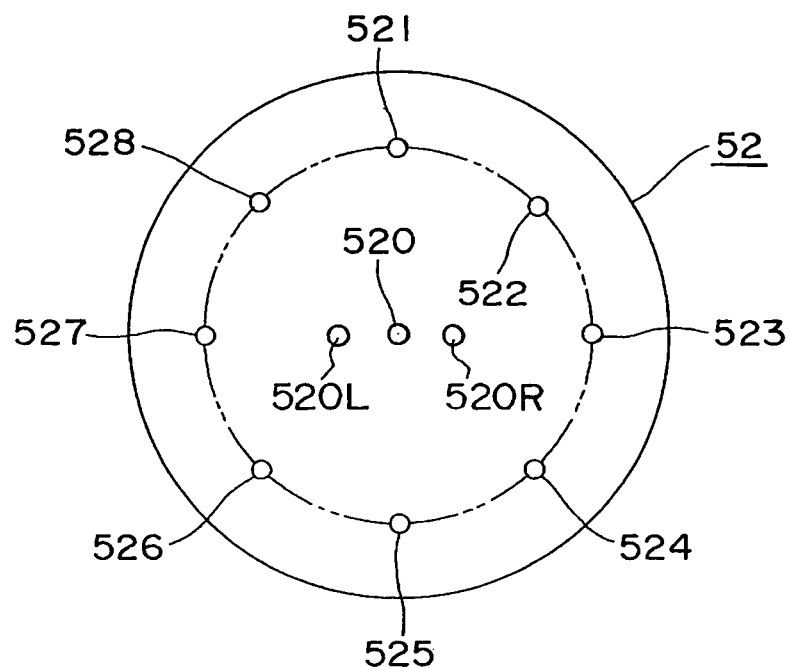
FIG. 6 is a plane view showing an arrangement state of pinholes of a mask plate shown in FIG. 2.

Each of the fixation light sources 510 (510L, 510R)-518 in FIG. 5 is disposed opposing to each of pinholes 520 (520L, 520R)-528 provided on the mask plate 52 as shown in FIG. 6. The biforate stop 431 rotates in conjunction with lightening of the fixation light sources 51.

Light from the fixation light sources 51 transmits the respective pinholes 520-528 of the mask plate 52 and is projected on the fundus Ef as the fixation targets through the dichroic mirror 53, the imaging lens 22, the focus lens 21 and the object lens 11. Therefore, pinhole images are formed and indicated as the fixation targets on the fundus Ef. The subject is visually fixed by viewing the fixation targets.

Visual fixation direction with respect to the optical axis O of the photographing optical system 20 is switched according to the lightening of any of the fixation light sources 510-518, thus it is possible to change sites of the fundus Ef which are expected to be observed and/or photographed. The fixation light sources 51 may contain any numbers of fixation lights which may be disposed at any shape, such as a cross, a vertical or horizontal line, a triangle, a pentagon or a regular hexagon etc.

For example, if the fixation light sources 510-518, in other words, eight octagon-shaped fixation light sources 511-518 around the fixation light source 510 are lightened sequentially, the biforate stop 431 is rotated every 45 degrees. If the fixation light sources 51 are lightened in a cross shape, the biforate stop 431 is rotated every 90 degrees and is rotated every 180 degrees if the fixation light sources 51 are lightened in a line, for example the fixation light sources 510, 513 and 517 are lightened as shown in FIG. 5.

[The Monitor Screen 80]

The monitor screen 80 is used to display a reference position mark for the respective alignment images corresponding to the lightening of the fixation light sources 51 (510-518) respectively.

For example, FIG. 10 is a view showing a reference position mark 54 for the alignment image corresponding to the central fixation light source 510 of the fixation light sources 51 (510-518).

In addition, reference marks for the other alignment images corresponding to the surrounding fixation light sources 511-518 of the fixation light sources 51 (510-518) are omitted and not shown in FIGS.

When the cornea apex is deviated from the optical axis 0 in photographing the surrounding parts of the fundus Ef, the reference marks for the surrounding alignment images indicate this deviation to the physician.

Thus, the physician may perform alignment adjustments easily even when photographing the surrounding parts. Therefore, the reference marks for the surrounding alignment images may be displayed on the monitor screen 80 in different positions corresponding respectively to presenting positions of the fixation targets switched by a presenting position switching device (a fixation target position selecting device operated via buttons 76-78 or a display frame 61).

The presenting position switching device used to control lightening positions of the fixation light sources 510-518 may be disposed at an arbitrary place and may be operated from the monitor screen 80 or buttons on a operation panel during observation and photographing in the present embodiment.

A part of the whole eye fundus Ef which should be photographed may be displayed at the center of the monitor screen 80 as a fundus image Er. The fundus image Er may be either a video or a still image. As shown in FIG. 3, the subject's eye E (left eye) is fixed by the fixation light source 510L according to the Law of Health and Medical Services for the Aged, an eye fundus image Ero corresponding to the central part of the posterior fundus is displayed animatedly on the monitor screen 80. Hereinafter, the fixation light sources 510L and 510R may also be simply referred to as the fixation light source 510.

Furthermore, on the monitor screen 80, besides the fundus image Er displayed animatedly, the display frame 61 positioned at a down-left corner (used also by the presenting position switching device) to display a part of the whole eye fundus Ef being observed or photographed, a brightness information frame 62 for the illumination light source (used also by a brightness adjustment virtual shift knob) and an information frame 63 relating to photographing light amount and the subject's information are properly disposed in the monitor screen 80 and may be configured or varied in initial settings or any arbitrary step of the ophthalmologic photographing apparatus.

Figure 7:
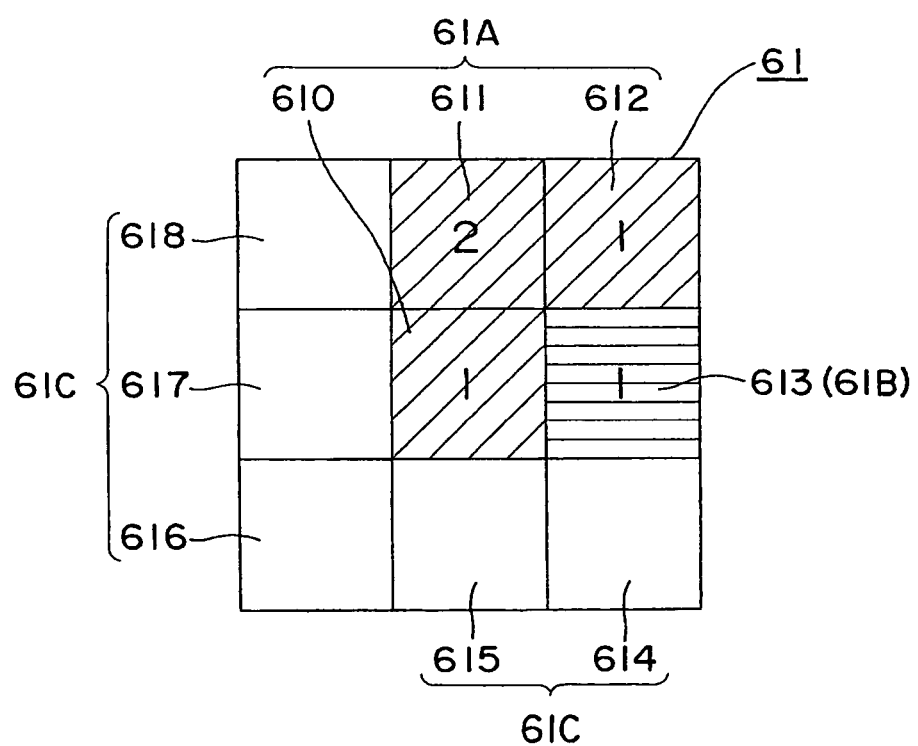
FIG. 7 is an explanatory view showing in detail an indication frame shown in FIG. 3.

As shown in FIG. 7, the display frame 61 includes 9 squares of a central square 610 and surrounding squares 611-618. The central square 610 corresponds to the central fixation light source 510 (or 510L, 510R), and the surrounding squares 611-618 corresponds respectively to the surrounding fixation light sources 511-518.

Thus, the physician may select the presenting positions of the fixation targets, that is, the part of the whole eye fundus Ef which should be photographed by selecting each of the squares 610-618 in the display frame 61 with a mouse or else. In addition, recognition pattern diagrams showing the fundus Ef schematically may be drawn in the display frame 61.

In a panorama photographing, a photographed part, a photographing part or an un-photographed part in the display frame 61 may be configured to be differentiated by visual viewing. Such differentiation may be configured by differentiating brightness or chroma saturation etc, for example, the photographing part may be set at relatively high brightness or low brightness, or with different chroma saturation or blinking as if it may be differentiated by visual viewing compared with the other parts.

As shown in FIG. 7, the photographed part 61A, the photographing part 61B and the un-photographed part 61C are differentiated by displaying each of them with slant lines representing "white or white outlined", horizontal lines representing "blinking" and no marks representing "low brightness or black", respectively.

In addition, in each of the squares 610-618, there is an Arabic numeral showing numbers of still images for each part photographed. For example, in FIG. 7, numeral 1 means that the corresponding part has been photographed once and numeral 2 for two times.

Furthermore, the central square 610 may be displayed with a letter "C" if the central fixation light source 510 is used, and accordingly it may be displayed with a letter "L" or "R" in relation to the subject's left or right eye E if the fixation light source 510L or 510R is used according to the Law of Health and Medical Services for the Aged.

Therefore, the photographing part is the blinking (horizontal lines) square 613 (61B) with a numeral 1 meaning that one image had been taken. Squares 61A (610, 611 and 612) are white or white outlined (slant lines) with numerals showing numbers of the still image photographed. Squares 641-618 are in low brightness or black (no marks) meaning that they are not photographed till now.

Thus, by displaying the photographing part 61B, un-photographed part 61C and photographed part 61A in each square as parts of the whole target panorama photographing image, the physician (photographer) may understand quite easily which part is being photographed (or observed) and which part will be photographed by taking each part as a panorama image.

Operations on the display frame 61 may be performed by clicking each of the squares 610-618 with a mouse to set fixation target positions (observing or photographing positions) corresponding to the respective fixation light sources 510-518 lightened. In addition, operations on the fixation target positions (observing or photographing positions) may also be performed from the operation panel, which will be described in detail with the operation panel hereinafter.

[The Controlling Device 9]

Hereinafter the controlling device 9 connected with various devices will be described according to FIG. 8.

The controlling device 9 includes a computer etc having a calculating section and a memory section. The controlling device 9 may be built in the main body of the ophthalmologic photographing apparatus, or coupled with an external controlling device, such as a computer.

The controlling device 9 is connected with the monitor 8, the still video recorder 7, the photographing TV camera 6A and the observing TV camera 6B.

The monitor 8 is built in the main body in the present embodiment; it may also be used together with an external monitor which may be connected with an external computer (a part of the controlling device 9).

In general, in order to process or record the photographed eye fundus images (ophthalmologic images), the controlling device 9 is connected with an external computer (not shown).

Furthermore, the controlling device 9 is connected with the operation device 5 and may be operated by various input signals from the operation device 5 according to predefined programs, respectively.

Although the controlling device 9 is connected with a determination/compensation circuit for determining/compensating various alignments in XYZ directions, a focus determination circuit, and controlling circuits and driving circuits thereof, detailed descriptions on them are omitted.

In addition, the controlling device 9 is configured to be controlled or operated by driving devices 21a, 91, 190a2, 200a and 201a.

Furthermore, the controlling device 9 is connected to a mode switching button 202 as a mode switching device for switching between an initial setting mode and an eye fundus photographing mode of the fundus camera.

An ophthalmologic apparatus (vision testing apparatus) such as a refractmeter or a subjective optometer may be connected to the controlling device 9 via a not shown computer (a first data inputting device) and the diopter data determined by the ophthalmologic apparatus may be transferred to the controlling device 9 together with the subject's ID.

In addition, the diopter data determined by the ophthalmologic apparatus (a diopter data inputting device, the vision testing apparatus), such as the refractmeter or subjective optometer, may be firstly stored in an IC card or a CF card and then inputted into the controlling device 9 via a data reading device (a second data inputting device).

The above mentioned first and second data inputting devices are referred to as a data inputting device 60, as shown in FIG. 2.

According to the various input signals from the aforementioned operation device 5, the controlling device 9 controls the still video recorder 7 and monitor 8 according to a predefined program.

Figure 8:
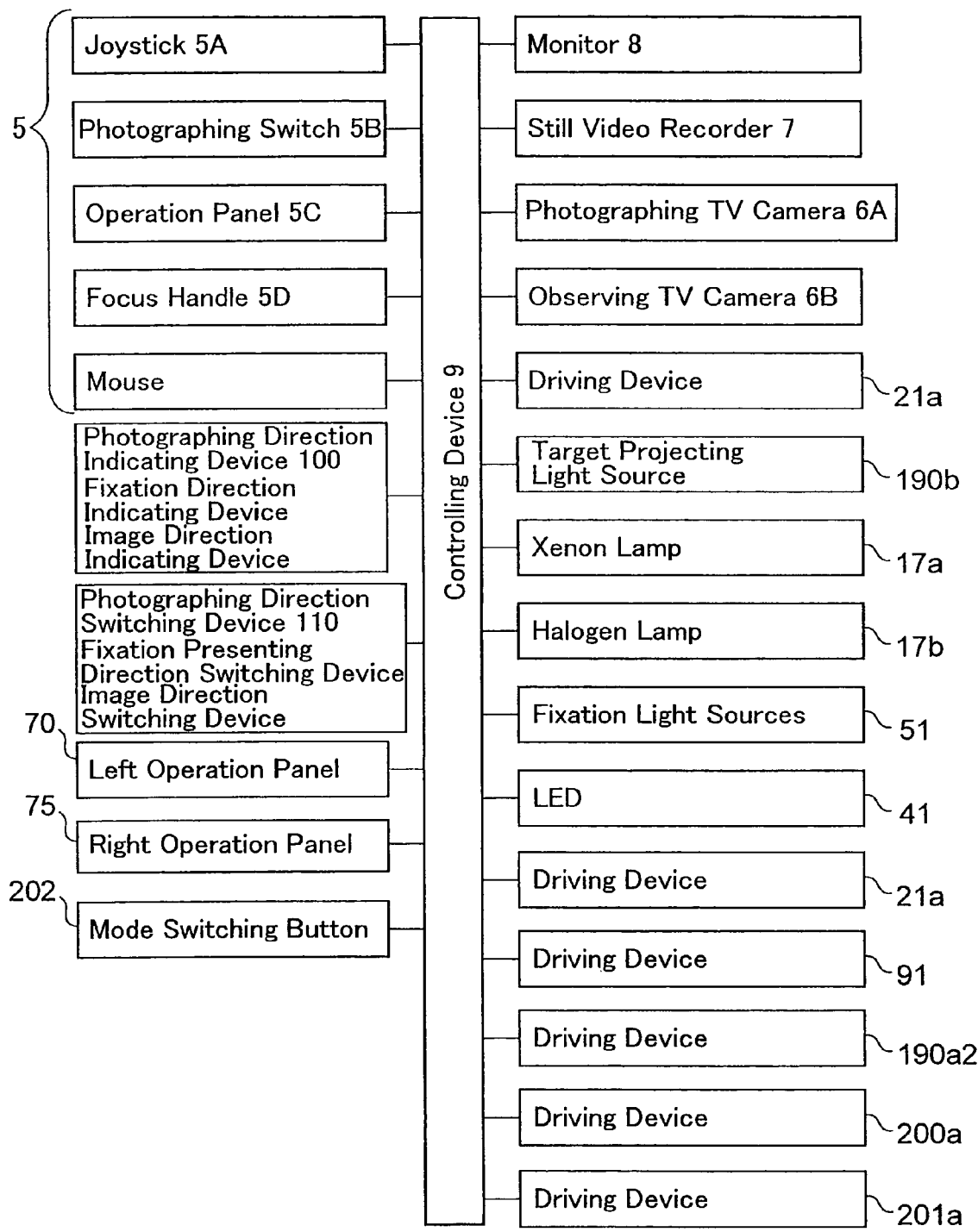
FIG. 8 is an explanatory view showing relationships of a controlling device of the fundus camera shown in FIG. 1.

A photographing direction indicating device 100 in FIG. 8 may be for example a fixation direction indicating device for controlling lightening positions of the fixation light sources 51 (510-518) in FIG. 5. The fixation direction indicating device may be controlled in conjunction with rotation controlling on the biforate stop 431 and the selecting device of the alignment reference mark 54.

In addition, the photographing direction indicating device (the fixation direction indicating device) 100 may be switched by a photographing direction switching device 110 (a fixation presenting direction switching device) to make its photographing indicating directions (fixation target presenting positions) bilaterally symmetric.

For the ophthalmologic apparatus including an image direction switching device for switching displaying an image in a bilaterally symmetric display on the monitor screen 80, it is preferable for the photographing direction switching device 110 to be the image direction switching device.

It is preferable to switch the photographing direction via the controlling device 9; it is also preferable to switch the fixation direction indicating device and the image direction indicating device via an electric switching device such that the photographing directions may be bilaterally symmetric.

In the present embodiment, it is an expedient treatment as shown in FIG. 8 that all indicating devices are connected to the controlling device 9 and controlled by respective driving devices according to signals from the controlling device 9.

Figure 9:
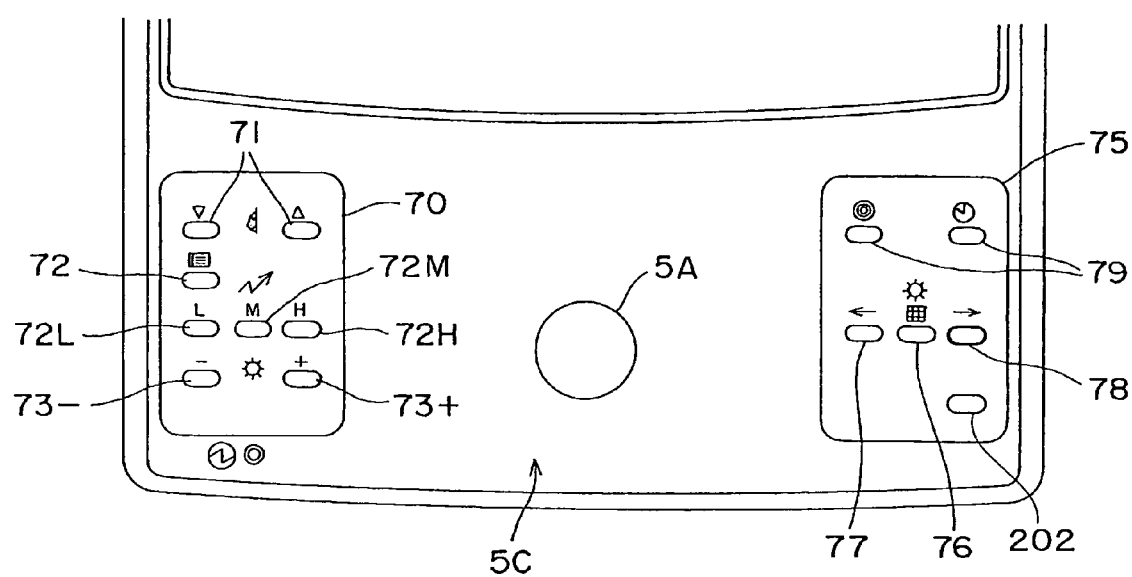
FIG. 9 is an explanatory view showing in detail an operation panel of the fundus camera shown in FIG. 1.

As shown in FIG. 9, the operation panel 5C includes the joystick 5A in the center, a left operation panel 70 and a right operation panel 75. The left operation panel 70 is provided with a pair of buttons 71 (marked with a downward arrow and an upward arrow respectively) with a human mark therebetween, a menu button 72 marked with a menu figure (M mark), a thunder flash mark, and buttons 72L, 72M and 72H marked respectively with letters L, M and H, and light amount adjusting buttons 73+ and 73− with a sun mark therebetween.

On the other side, there are 3 buttons (the photographing direction indicating device and also the photographing direction switching device) for selecting photographing position lined up in the center of the right operation panel 75. A button 76 in the center is a button for returning the fixation target (corresponding to the fixation light source 510) to the central part. A button 77 with a leftward arrow is a button for moving the presenting position of a fixation target leftward and a button 78 with a rightward arrow is a button for moving the presenting position of a fixation target rightward.

In addition, it is preferable for the central button 76 to return the fixation target from 510R to 510L according to the Law of Health and Medical Services for the Aged. Buttons 79 are switches used for a timer and fluorescent photographing.

Furthermore, in a panorama photographing, operation buttons 76~78 may be provided with functions such as to move sequentially fixation targets according to a preliminarily programmed method.

Fox example, the aforementioned operation buttons 76~78 may function as panorama mode selecting buttons such that after the fundus camera finishes photographing on the central part controlled by the button 76, by pressing the button 77 or 78 the fundus camera may be switched into a peripheral photographing mode and the biforate stop 431 for peripheral photographing may be inserted, making photographing on the fundus Ef corresponding to the square 611 possible.

In addition, the presenting positions of the fixation targets are changed sequentially according to rotation directions of the biforate stop 431 determined by the button 77 or 78. Accordingly, the alignment reference mark 54 is also changed to be displayed at a predetermined position on the monitor screen 80 by the reference mark selecting device in conjunction with the changing of the presenting positions of the fixation targets, thus the target parts may be observed and/or photographed as the fundus images 1-8.

Thus, when the posterior part of the fundus Ef is photographed, the fixation light source 510 in the center is lightened and accordingly the fixation target of the pinhole 520 is presented in the subject's eye E, it is therefore possible to photograph the central part (i.e., the posterior part of the fundus Ef) as the fundus image Ero.

When the surrounding parts of the fundus Ef are photographed, the fixation light sources 511-518 corresponding to the surrounding parts of the fundus Ef to be photographed are lightened and accordingly the fixation targets of the pinholes 521-528 are presented in the subject's eye E. Together with the animated image showing the fundus Ef displayed on the monitor screen 80, the focus target images 191a and 191b, the alignment reference mark 54 and alignment images 421 corresponding to the target position are also displayed on the monitor screen 80.

Thus, the physician may perform focusing by adjusting the focus target images 191a and 191b until they are vertically lined up, or perform alignment by adjusting the alignment images 421 until they are overlapped to one image positioned in the center of the alignment reference mark 54.

If the operation distance W (Z direction) and positions along XY direction (perpendicular to the optical axis O) are appropriate, the alignment images 421 from the emitting end 42a are completely overlapped in the center of the alignment reference mark 54 displayed on the monitor screen 80 together with the fundus image Er, as shown in FIG. 10. If the alignment is deviated from the appropriate position, the alignment images 421 from the emitting end 42a are formed splitting.

It is therefore for the physician to perform alignment adjusting by confirming the overlapping or splitting information of the alignment images 421 based on the alignment light.

[Operations]

One example of observing and photographing procedures using the fundus camera with the aforementioned configuration is described.

(1) Initial Settings of the Fundus Camera

Before photographing, the physician may set the non-mydriatic fundus camera to an eye fundus photographing mode by pressing the mode switching button 202 which is the mode switching device and perform the initial settings for the fundus camera.

The initial settings may be performed from operations on the monitor screen 80. For example, when the menu button 72 is pressed, there is displayed a menu window. Similar to initial settings of a common camera, such settings as a classification of necessary information and unnecessary information, display range settings of the monitor screen 80, reference value settings of the photographing light amount, selections on external storage devices or photographing devices for connecting are performed.

In addition, it is possible to select fixation targets between internal and external fixation targets, and the internal fixation targets may be displayed hierarchically for selecting if the internal fixation targets are used.

The buttons 72L and 72H may be set as the operation device 5 to move a cursor on the monitor screen 80 for selecting a menu. The cursor is moved to the menu by operating the buttons 72L and 72R. By pressing the button 72M, the menu will be selected. The photographing direction switching window is selected according to the menu selection.

Figure 11:
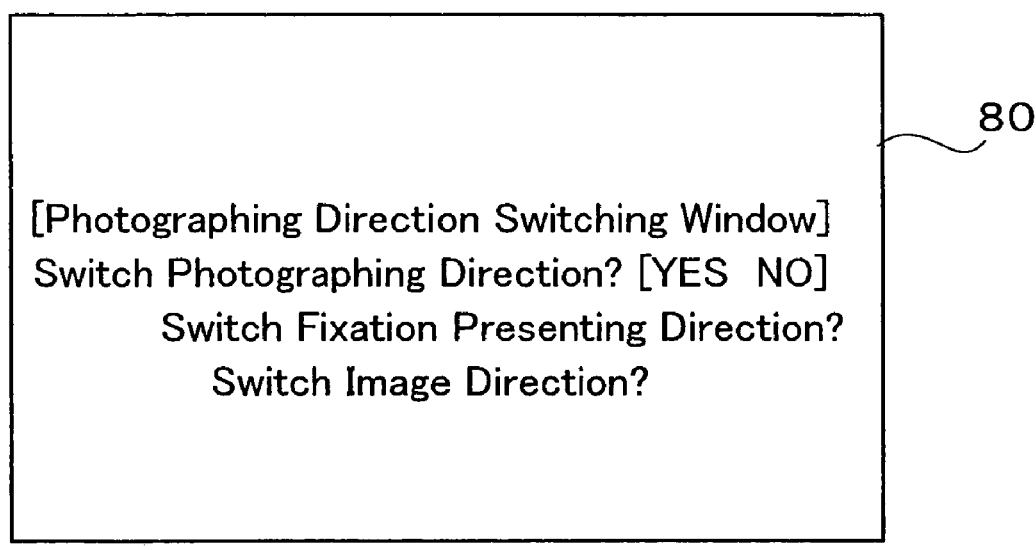
FIG. 11 is an explanatory view showing the monitor screen in which a switching process by which peripheral regions of the fundus are photographed is displayed.

FIG. 11 shows an example of the monitor screen 80 in which the photographing direction switching window is displayed. In FIG. 11, if the photographing direction is switched to "YES" (meaning a reversed direction), the fixation presenting direction switching device is reversed and switched to a reverse side. The fixation target presenting directions are bilaterally reversed or not reversed according to selection of the fixation presenting direction switching device (photographing direction switching) or not. In addition, an image is displayed on the screen bilaterally reversed if the image direction switching is selected. The image direction device may be set from the monitor screen 80 or from a computer setting screen if an external computer is used.

(2) Eye Fundus Photographing Mode

When a power switch (not shown) is set ON, the controlling device 9 displays a message window for inputting a subject's data such as the subject's ID or name, sex, age and address information etc on the monitor screen 80, or a monitor screen (not shown) of the external computer connected to the controlling device 9. Following the message window, the physician inputs the subject's data to the controlling device 9 through a not shown computer, an IC card reader, a subject's ID reader, or to the external computer connected to the controlling device 9.

After the subject's data are inputted, the controlling device 9 determines whether or not the subject's diopter data are existed in the external computer connected to the controlling device 9 and executes immediately an alignment mode if the subject's diopter data are existed. If the subject's diopter data are not existed, the controlling device 9 displays a message window demanding for the input of the subject's diopter data on the monitor screen 80 or monitor screen of the external computer (not shown) connected to the controlling device 9.

According to the demand, the physician operates the external computer (not shown) connected to the controlling device 9 and sends a diopter data transfer demand to the ophthalmologic apparatus such as a refractmeter or a subjective optometer. The diopter data will be transferred from the external ophthalmologic apparatus to the external computer (not shown) connected to the controlling device 9 if there is the diopter data existed in the external ophthalmologic apparatus such as a refractmeter or a subjective optometer.

While if there is no diopter data existed in the external ophthalmologic apparatus, the controlling device 9 executes the alignment mode anyway.

On the other hand, when the power switch (not shown) is set ON, the controlling device 9 controls the driving device 91 to insert the auxiliary lens 90 into the light-receiving optical path of the photographing optical system 20 between the focus lens 21 and the half-silvered mirror 46 and sets the observing TV camera 6A of the observing optical system 30 to a prepared state for observing the anterior part of the subject's eye E and ready for observing the pupil Ea of the subject's eye E.

In order to observe and photograph the fundus Ef, nonmydriatic fundus camera is set to the fundus photographing mode by pressing the mode switching button 202 which is the mode switching device and optically aligned such that the fundus camera and the subject's eye E are kept in the operation distance W appropriate for the fundus photographing.

After the optical alignment of the fundus camera (main body) with respect to the subject's eye E is finished, the controlling device 9 controls the driving device 91 to withdraw the auxiliary lens 90 from the light-receiving optical path and determines whether the subject's diopter data are existed in the external computer (not shown) connected to the controlling device 9.

(i) In a Case when the Diopter Data are Existed (A) Insertion of the Diopter Compensation Lens 200 or 201 According to Focusing Range Determination Then the controlling device 9 determines whether the diopter data are within the focusing range of the focus lens 21 and executes the observing mode of the fundus Ef if the diopter data are within the focusing range.

If the diopter data relating to the subject's eye E surpass the focusing range of the focus lens 21, the controlling device 9 determines whether the diopter data relating to the subject's eye E belong to severe myopia or hyperopia.

In a case when the diopter data belong to severe myopia, the controlling device 9 controls the driving device 200*a* to insert the minus diopter compensation lens 200 into the light-receiving optical path of the photographing optical system 20 between the focus lens 21 and the half-silvered mirror 46; while in the other case when the diopter data belong to severe hyperopia, the controlling device 9 controls the driving device 201*a* to insert the plus diopter compensation lens 201 into the light-receiving optical path of the photographing optical system 20 between the focus lens 21 and the half-silvered mirror 46.

After that, the controlling device 9 executes the observing mode of the fundus Ef.

(B) Alignment

When the fundus Ef is observed, the fundus Ef is illuminated with the infrared light by the illumination optical system 10. When an identical light source is used, it is preferable to insert an appropriate optical filter into the illumination optical system 10 and select the infrared light only. In the present embodiment, the halogen lamp 17*b* is used as the observing light source with the IR filter (infrared filter) 18 inserted.

The reflecting infrared light is formed into the fundus image Er on the photographing element CCD 6*b* of the observing TV camera 6B by the observing optical system 30.

The fundus image Er formed on the photographing element CCD 6*b* is displayed on the monitor screen 80 via the controlling device 9 as a black-and-white animation image.

At this moment, the controlling device 9 inserts the stick mirror or target stick 190*a* into the optical path of the illumination optical system 10 and lightens the target projecting light source 190*b*.

In addition, the stick mirror or target stick 190*a* is projected on the fundus Ef by the illumination light from the illumination optical system 10 as a shadow. Light from the target projecting light source 190*b* transmits through the pinhole plate 190*c*, the lens 190*d*, the prism lens 190*e*, the focus target plate 190*f*, the biforate stop plate 190*g* and the lens 190*h* to the stick mirror 190*a*, and is reflected from the reflecting surface 190*a*1 of the stick mirror 190*a* to be projected on the fundus Ef of the subject's eye E through the relay lens 13, the perforated mirror 12 and the object lens 11 as the focus target light.

Under such circumstance, the physician operates the joystick 5A to move the main body 1 with respect to the subject's eye E, performing continuously the alignment of the main body 1 with respect to the subject's eye E by viewing the monitor screen 80 for observing the fundus Ef.

(C) Focus Control

While if the fundus Ef of the subject's eye E and the reflecting surface of the stick mirror 190*a* are not in conjugation the focus target image formed from the focus target light is generally split into two focus target images 191*a* and 191*b* bilaterally as shown in FIG. 12, even if the alignment of the main body 1 with respect to the subject's eye E is completed.

Figure 3A:
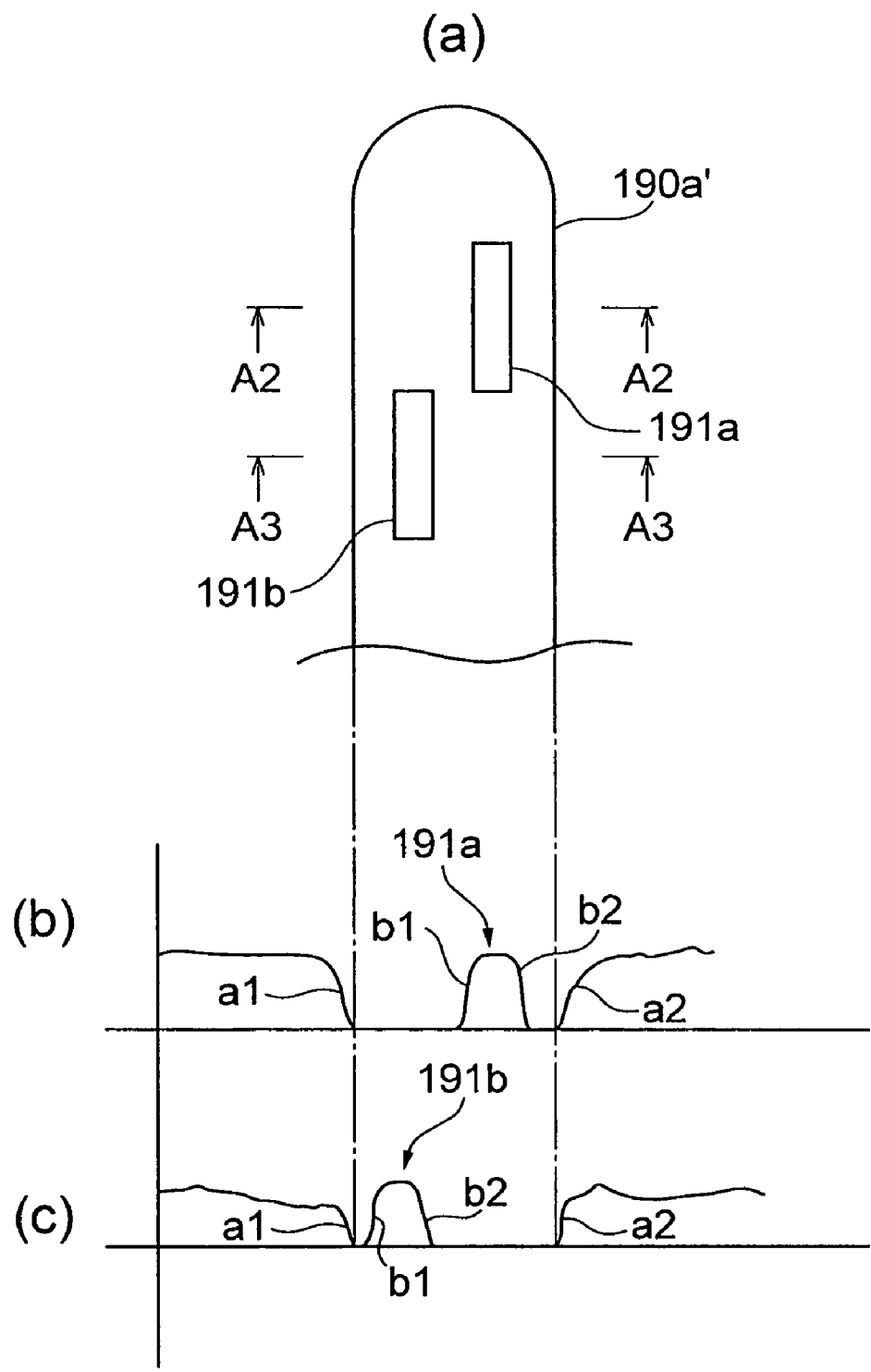
FIG. 3A (a) is an explanatory view showing a stick mirror and focus-target images in FIG. 3 in a non-focused state.

Under this condition, a mirror image 190*a*' of the stick mirror 190*a* and the surroundings of the focus target images 191*a* and 191*b* are in a defocused state as shown in FIG. 3A (a). In other words, the apparatus is generally not focused even if the alignment is OK.

At this moment, if a given part where the mirror image 190*a*' and focus images 191*a* and 191*b* are formed on the photographing element CCD 6*b* is scanned, a falling portion a1 and rising portion a2 of the peripheral part of the mirror image 190*a*', a rising portion b1 and falling portion b2 of the peripheral part of the focus target images 191*a* and 191*b* respectively are in a little bit flaggy state. Therefore, it is clear that the apparatus is not focused.

Thus, after the alignment is completed, the controlling device 9 determines that the apparatus is not focused and thus the focus direction according to states of the two bilaterally split focus target images 191a and 191b, the falling portion a1 and rising portion a2, and the rising portion b1 and falling portion b2 from the photographing element CCD 6b; and controls the driving device 21a, e.g. a pulse motor, to move the focus lens 21 along the Z direction of the observing optical axis, making the fundus Ef of the subject's eye E and the photographing element CCD 6b of the observing TV camera 6B in conjugation.

In conjunction with this, the focus target projecting optical system 190 is moved toward the optical axis of the illumination optical system 10, making the focus target plate 190f and the fundus Ef in conjugation.

Figure 3B:
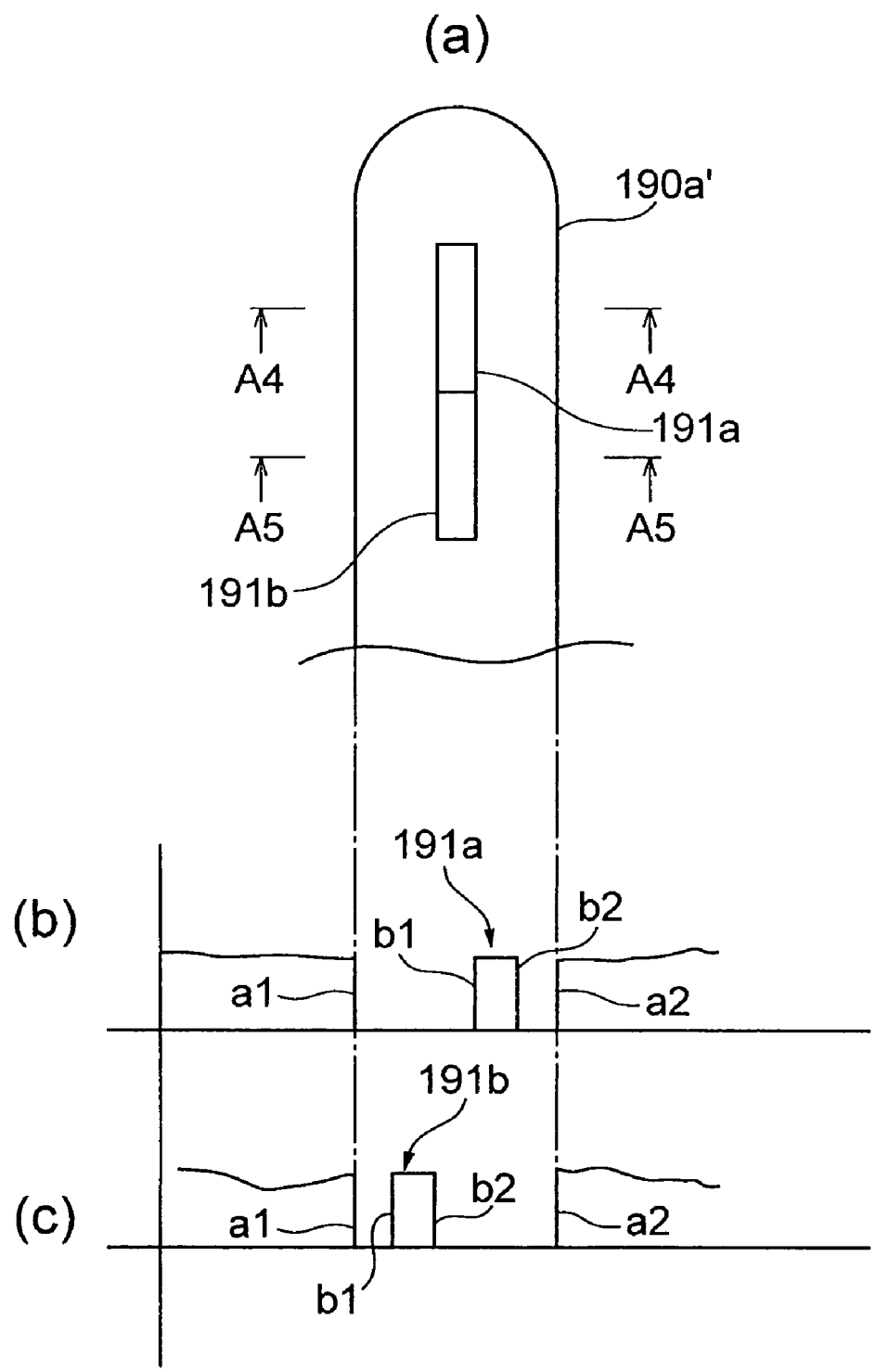
FIG. 3B (a) is an explanatory view showing the stick mirror and focus-target images in FIG. 3 in a focused state.

When the focus target images 191a and 191b are lined up vertically into one according to the aforementioned focusing, the peripheral parts of the mirror image 190a' of the stick mirror 190a and focus target images 191a and 191b will be sharp and clear as shown in FIG. 3B (a).

At this moment as shown in FIGS. 3B (b) and 3B (c), if the given part where the mirror image 190a' and focus images 191a and 191b are formed on the photographing element CCD 6b is scanned, the falling portion a1 and rising portion a2 of the peripheral part of the mirror image 190a', the rising portion b1 and falling portion b2 of the peripheral part of the focus target images 191a and 191b respectively are of a vertical shape. Therefore, it is clear that the apparatus is focused.

Thus, the controlling device 9 determines that the apparatus is focused according to that the two bilaterally split focus target images 191a and 191b are lined up vertically into one image, and that the falling portion a1 and rising portion a2, and the rising portion b1 and falling portion b2 are of a vertical shape; and stops the driving device 21a shifting the focus lens 21 along the optical axis.

It will happen that sometimes such focus operation (auto focus) will not end normally and sometimes the focus state is not satisfied after focusing. Thus the controlling device 9 is configured that it will not perform a next focus operation after the focus operation is performed once with respect to one alignment so that the physician may perform focusing manually.

Therefore, when the auto focus is not finished normally, or the focus state is not satisfied after focusing, it is possible that the focus operation may be performed manually by operating the focus handle 5D after the auto focus.

After the focus operation is completed, the completed focus operation state is displayed on the monitor screen 80, which notifies the physician that the photographing is possible.

(D) Photographing

The physician presses the photographing switch 5B to perform photographing according to the notification.

According to the operation on the photographing switch 5B, the controlling device 9 controls the driving motor 190a2 to withdraw the stick mirror 190a from the illumination optical path and makes photographing light source, the xenon lamp 17a emitting visual light to illuminate the fundus Ef of the subject's eye E via the illumination optical system 10.

The reflecting light from the fundus Ef depending on the illumination is guided to the photographing element CCD 6a of the photographing TV camera 6A of the photographing optical system 20, forming the fundus image Er as a color still image on the photographing element CCD 6a of the photographing TV camera 6A.

The fundus image Er formed on the photographing TV camera 6A containing necessary image information is not only recorded in the still video recorder 7 but also displayed on the monitor screen 80 as a still image. The necessary image information may include the patient name, photographing date, photographing time and the photographer name etc, while the photographing location information necessary for replaying the panorama image, and information concerning numbers of photographs taken relating to the photographing site etc may also be included.

(ii) In a Case when the Diopter Data are not Existed

The controlling device 9 performs the focus control described in (C) after the alignment described in (B) is completed. At this moment, the controlling device 9 controls the driving device 21a to rotate normally or reversely, shifting the focus lens 21 along the optical axis within the focusing range (for example, from +12D to −13D).

When the focus target images 191a and 191b are lined up vertically into one image within the focusing range (for example, from +12D to −13D) according to the shifting (focusing) of the focus lens 21, the mirror image 190a' of the stick mirror 190a and focus target images 191a and 191b will be sharp and clear as shown in FIG. 3B (a).

On the other hand, if the focus target images 191a and 191b (split images) can not be lined up into one image after focusing, it means that the subject's eye E is of severe myopia or hyperopia.

In this occasion, the controlling device 9 determines which of the minus diopter compensation lens 200 and the plus diopter compensation lens 201 is to be inserted according to the blurring state of the mirror image 190a' of the stick mirror 190a and the splitting state of the focus target images 191a and 191b, etc.

In other words, the controlling device 9 determines that the fundus camera is not focused according to the vertical splitting state of the two focus target images 191a and 191b as described in (C) and the states of the falling portion a1 and rising portion a2, and the rising portion b1 and falling portion b2 from the photographing element CCD 6b and that the subject's eye E is of severe myopia or hyperopia according to the defocused extent.

The controlling device 9 controls the driving device 200a to insert the minus diopter compensation lens 200 into the light-receiving optical path of the photographing optical system 20 between the half-silvered mirror 46 and focus lens 21 if the subject's eye E is of severe myopia, or the driving device 201a to insert the plus diopter compensation lens 201 into the light-receiving optical path of the photographing optical system 20 between the half-silvered mirror 46 and focus lens 21 if the subject's eye E is of severe hyperopia, and continues to perform the focus control as described in (C).

After the focus operation as described in (C) is completed, the photographing as described in (D) is performed.

In addition, it is possible for the controlling device 9 to make a focus by controlling the driving device 21a to rotate normally or reversely to move the focus lens 21 along the optical axis and to determine the shifting direction of the focus lens 21 according to the focusing state variation.

Furthermore, it is also possible for the controlling device 9 to determine whether the completed focusing state is within the feasible focusing range of the focus lens according to the focus state (positions, or relative positions of plural lenses if the focus lens is made from a combination of plural lenses) and focusing state (positions of the split focus target images, rising and falling states of the peripheral parts of the image from the photographing devices).

(iii) Others

In the aforementioned embodiment, though the fundus camera has such a configuration that the diopter data are transferred to an external computer (not shown) connected to the controlling device 9 from an ophthalmologic apparatus (vision testing apparatus) such as a refractmeter or a subjective optometer and the minus diopter compensation lens 200 or plus diopter compensation lens 201 is determined to be inserted into the optical path by using the diopter data, it is not limited to such configuration.

For example, the diopter data (diopter information) may be manually inputted to an external computer (not shown) connected to the controlling device 9.

In addition, the controlling device 9 is configured to insert automatically either the minus diopter compensation lens 200 or the plus diopter compensation lens 201 into the optical path according to a pre-determination which one of them should be inserted. It is also preferable to insert manually the diopter compensation lenses into the optical path by releasing the automatic mode for inserting automatically the diopter compensation lenses.

In this case, it is preferable to provide the automatic mode in which the diopter compensation lenses are inserted automatically into the optical path and the manual mode in which the diopter compensation lenses are inserted manually into the optical path as the fundus photographing modes switched by the mode switching button 202 and it is possible to switch between the automatic mode and manual mode by the mode switching button 202.

Although the present invention has been described in relation to its preferred embodiment and drawings, it is to be understood that other possible modifications and/or variations made without departing from the spirit and scope of the present invention will be comprised.

What is claimed is:

1. A fundus camera, comprising:
   an illumination optical system for projecting an illumination light to a fundus of a subject's eye;
   a photographing device for photographing the fundus; and
   a light-receiving optical system for guiding the reflected illumination light from the fundus to the photographing device, which includes a focus lens disposed in a light-receiving optical path for focusing the photographing device with respect to the fundus and a diopter compensation lens configured as being inserted into or withdrawn from the light-receiving optical path;
   a controlling device for determining whether a feasible focusing range of the focus lens is surpassed or not; and
   a driving device for inserting the diopter compensation lens into or withdrawing the diopter compensation lens from the light-receiving optical path,
   wherein the controlling device controls the driving device to insert into the light-receiving optical path the diopter compensation lens with a suitable diopter scale making the focus lens focus feasibly if the feasible focusing range of the focus lens is surpassed.

2. The fundus camera set forth in claim 1, further comprising a data input device for inputting diopter data determined in an ophthalmologic apparatus,
   wherein the controlling device controls the driving device to insert into the light-receiving optical path the diopter compensation lens with a suitable diopter scale making the focus lens focus feasibly if the diopter data surpass the feasible focusing range of the focus lens.

3. The fundus camera set forth in claim 1, wherein the controlling device determines not only a moving direction of the focus lens based on focusing state variations relating with driving of the focus lens but also whether the feasible focusing range of the focus lens is surpassed when the focusing state is completed, and controls the driving device to insert into the light-receiving optical path the diopter compensation lens with a suitable diopter scale making the focus lens focus feasibly if the feasible focusing range of the focus lens is surpassed.

4. The fundus camera set forth in claim 1, wherein the controlling device controls the driving device to insert into the light-receiving optical path the diopter compensation lens with a suitable diopter scale making the focus lens focus feasibly if a limitation of the feasible focusing range of the focus lens is reached.

5. The fundus camera set forth in claims 1 further comprises a mode switching device for switching between an automatic mode in which the diopter compensation lens is inserted automatically into the light-receiving optical path and a manual mode in which the diopter compensation lens is inserted manually into the light-receiving optical path, wherein the diopter compensation lens with a suitable diopter scale making the focus lens focus feasibly is manually inserted into the light-receiving optical path according to switching of the mode switching device if the feasible focusing range of the focus lens is surpassed.

* * * * *

UNITED STATES PATENT AND TRADEMARK OFFICE
CERTIFICATE OF CORRECTION

| | |
|---|---|
| PATENT NO. | : 7,377,642 B2 |
| APPLICATION NO. | : 11/498728 |
| DATED | : May 27, 2008 |
| INVENTOR(S) | : Mutsutaka Ishihara et al. |

It is certified that error appears in the above-identified patent and that said Letters Patent is hereby corrected as shown below:

Title Page, Item (73) Assignee: Kabushiki Kasisha Topcon, Tokyo (JP) should read --Kabushiki Kaisha Topcon--.

Signed and Sealed this

Second Day of December, 2008

JON W. DUDAS
*Director of the United States Patent and Trademark Office*